United States Patent [19]

Fox et al.

[11] Patent Number: 4,898,328

[45] Date of Patent: Feb. 6, 1990

[54] EMANATOR FOR VOLATILE LIQUIDS

[75] Inventors: Rodney T. Fox, Cottingham; Philip W. Goreham, Beverley, both of Great Britain

[73] Assignee: Reckitt & Colman Products Limited, London, Great Britain

[21] Appl. No.: 96,116

[22] Filed: Sep. 11, 1987

[30] Foreign Application Priority Data

Sep. 12, 1986 [GB] United Kingdom ............... 8622046

[51] Int. Cl.$^4$ ............................................. A61L 9/04
[52] U.S. Cl. ........................................ 239/6; 239/34; 239/35
[58] Field of Search ................ 239/35, 44, 47, 49, 239/57, 34, 6; 428/447, 452

[56] References Cited

U.S. PATENT DOCUMENTS

| | | | |
|---|---|---|---|
| 2,239,628 | 4/1941 | Seki | 239/44 X |
| 3,858,807 | 1/1975 | Rabussier et al. | 239/57 X |
| 3,874,986 | 4/1975 | Browall | 428/315.9 |
| 4,127,127 | 11/1978 | Wong | 428/449 X |
| 4,360,554 | 11/1982 | Campbell | 428/91 |
| 4,444,662 | 4/1984 | Conover | 210/500.41 |

Primary Examiner—Andres Kashnikow
Attorney, Agent, or Firm—Frederick H. Rabin

[57] ABSTRACT

A device for dispensing a volatile liquid as a vapor includes a porous support of natural or synthetic woven or non-woven fibre, porous glasses, porous plastics (optionally in film form), parchment, leather or rubber provided with an organopolysiloxane material which serves to close the pores of the support to the passage of liquid but permits the passage of vapour from the liquid. The volatile liquid is a perfume, insecticide, insect repellant, insect attractant, higher animal repellant, corrosion inhibitor, a germicidal agent or a medicament. A space treatment vapor emanating device is thus provided the external surface of which device is dry to the touch.

39 Claims, 1 Drawing Sheet

EMANATOR FOR VOLATILE LIQUIDS

This invention is concerned with improvements in means for dispensing liquid substances as vapours from containers thereof.

Means for slow release of vapour from containers of liquid are well known at least in the field of air fresheners and insecticides.

Commonly, a suitable substrate such as cellulose wadding impregnated with, say, perfume oil and/or volatile liquid insecticidal compositions is supported on a frame and at least partly coverable by a structure limiting exposure of the wad to atmosphere so to give control over the extent of treatment of the environment by a user. Such arrangements sometimes give little or no control over rate of use by the user and certainly there is no indication of when the pad is exhausted, that is when it has become ineffective although still possessing an odour or discolouration due to the perfume or insecticide.

Alternatively, wicks immersed at one end in liquid contained in a clear bottle are adjustably exposed to atmosphere at the other end wherefrom the vapour emanates in well controllable fashion with an adjustable wick. The rate of usage is high hence diluted liquids are necessary which leads to relatively large bottles. In addition such arrangements are generally closable by a cap and there is danger of spillage if left unattended without a cap.

More recently a rupturable sachet of perfume has appeared on the market which sachet is contained in an outer sachet both being at least translucent. Such sachet combination is mounted on a suitable framework optionally assisting rupture of the inner sachet. These devices depend for shelf life upon impermeability of the rupturable inner sachet membrane. Extreme care needs to be exercised in formulating a composition so that leakage during storage does not occur and fractionation of liquid does not occur during use through the outer membrane selected. There is a clear end-of-life indicator when the liquid is exhausted.

It has been proposed to evaporate volatile treatment liquid through a solid web of silicone material acting as a liquid phase barrier. Whilst several advantages accrue from the use of such silicone barriers, the material is expensive and consequently inflates the cost of devices incorporating relatively great thicknesses of solid silicone.

We have now found that it is possible to effect slow release of vapour from liquids contained in a normally leak proof container at substantially linear rates without recourse to the excessive use of silicone.

Accordingly, the present invention provides a device for dispensing a volatile liquid as a vapour and includes a porous support provided with at least one cross-linked organopolysiloxane material which serves to close the pores of the support to passage of liquid and to permit the passage of vapour.

The device dispenses a contained liquid substance as a vapour. The organopolysiloxane material may be applied as a continuous or discontinuous film on the surface of the support and/or impregnated at least partly into the body thereof. It is sufficient that the pores of the substrate be so filled or closed with the organopolysiloxane that liquid per se cannot leak through the application.

The porous support may be in the form of a tube which is optionally closed ended to form a hollow container, or open-ended in the sense that liquid can flow through the tube in either direction under the influence of gravity or via pumping or otherwise. Alternatively, the porous support may be in the form of a sheet, web or bed, that is a structure that can act as a wall or part thereof and across a relatively short dimension of which is located the egress path of substance changing from liquid to vapour.

The porous support may be fashioned of natural or synthetic materials. Synthetic materials with hydroxyl groups in their structure are preferred. By way of example woven and/or non-woven natural or synthetic fibers in the form of webs or batts may be used. Wet laid fibrous products of the general class paper products, viz paper of all sorts, in particular glassine, cardboards, felts and the like may also be used as may parchments, leather and rubbers, sintered glass, porous plastics, plastics films and microporous plastics such as sintered polyolefins for example sintered polyethylene, sintered polyurethane. Care should be exercised in a choice of rubber as porous support because some contain components which inhibit curing of organopolysiloxanes. Also useful are the open pored plastics materials in cut block or film form produced from a blend of polymer(s) and a leachable material, such as a salt, followed by leaching out the compound with water or other suitable solvent to form a porous block or film as desired.

By "porous" as used herein is meant a structure which, lacking the organopolysiloxane material, can transmit liquids as such, albeit slowly, so that both sides can be wetted by the liquid.

A quick and simple method has been devised for testing the substrates useful in the present invention, the so-called "Oil Absorbency Test" to gauge the absorptive capacity of the porous support as substrate. In outline the test is conducted as follows:

"Oil Absorbency Test"

Accurately weigh into a Petri dish or similar approximately 4 g ($W_1$) of mineral oil of viscosity at 25° C. 95 mm$^2$/S(=Cst) ($\pm$10 mm$^2$S). Place two small pieces of the porous support under test, say, a paper 2.5 inch square in the dish. Allow to stand for approximately 5 minutes, that is until the porous support is saturated. Pour the unabsorbed oil into a tared vessel and accurately weigh it ($w_2$). The percentage oil absorbed is calculated viz:

$$\frac{W_1 - W_2}{W_1} \times 100 = \%\text{age oil absorption}$$

Suitable substrates have oil absorbency in the above test of at least 10%. Preferably the said oil absorbency is 17% to 50%. Typical oil absorbency values for some papers are:

|  | Oil absorbency |
| --- | --- |
| Toilet tissue 2-ply | 63% |
| Kitchen roll | 60% |
| Blotting paper (136 gm$^{-2}$) | 49% |
| KLEENEX* tissue 2-ply | 44% |
| WHATMAN* filter paper No 4 | 32% |
| WHATMAN* filter paper No 6 | 27% |
| Correspondence paper (77 gm$^{-2}$) | 17% |
| Kraft paper (brown) | 15% |
| Tracing paper | 12.5% |

| | Oil absorbency |
|---|---|
| Blue tissue paper | 12.5% |

The words asterisked are Trade Marks.

The organopolysiloxane material is preferably a silicone elastomer as distinct from a silicone oil or a silicone resin. Optionally, the organopolysiloxane material may contain a proportion of resin and/or oil.

Generally, the organopolysiloxane materials are produced from prepolymers, herein sometimes referred to as oligomers, via room-temperature vulcanisation or a low temperature vulcanisation, that is at temperatures of up to 150° C. applied for from a few, say, 5–10 seconds to 1 to 2 hours duration optionally in the presence of catalysts.

The prepolymers or oligomers have intermediate molecular weight and contain from a few hundred to a few thousand, for example up to 3000 polysiloxane units in substantially linear arrangement. Such intermediate molecular weight oligomers have viscosity values of up to 1,000,000 mm$^2$/s (=Cst); more particularly in the range 100–1,000,000 mm$^2$/s (=CSt) at 25° C. Preferably, the oligomers have viscosity of up to 20,000 mm$^2$/s(=Cst) at 25° C. It has been found that some components of the prepolymers useful in the present invention exhibit viscosities well below 100mm$^2$/s.

Preferably, the organopolysiloxane material is produced via a vulcanisation or cure reaction of a two-component mixture one of which separately supplied components containing the catalyst as necessary. Alternatively the catalyst may be added following mixing of the components.

Characteristically a silanol-terminated silicone polymer is one oligomer and a hydride-functional siloxane is used to cross-link it catalytically using organometallic tin compounds, for example soaps or tetraalkyltin compounds as catalyst in a condensation reaction. In that case the oligomeric silanol preferably contains not less than two hydroxyl groups per molecule located on different silicon atoms therein. The hydride- functional siloxane has not less than one reactive hydrogen atom, for every three silicon atoms therein.

Alternatively, the oligomer has reactive vinyl or allyl groups and undergoes an additional reaction with the sort of hydride-functional siloxane mentioned above in the presence of platinum or rhodium halides and complexes as catalyst to produce the organopolysiloxane elastomer.

The organopolysiloxane material may be applied to the mechanical support from an aqueous emulsion, or from solution in a hydrocarbon solvent. Alternatively, the organopolysiloxane material may be applied from a solventless system or produced in situ by curing the separately supplied oligomers or prepolymers in situ.

Application may be by doctor blade, air knife coaters, roller coaters (as for example with solvent systems in particular) that use either ground steel or rubberised rolls for the purpose.

To achieve good adhesion and/or in some cases where the thickness of the porous support is relatively great, and would consequently absorb excessive amounts of elastomer, application of elastomer, in whatever form is preceded by a first or primer coating. Such first coat or primer coat is usually of a silicone based often adhesive material and its function is either to seal the surface, give good adhesion or to achieve a good flow out of the subsequent coating(s) or a combination of these. Where the surfaces of the porous support are particularly inert as for example with certain polyolefin films and other structures, corona pretreatment may have to be resorted to for the sake of good adhesion.

Aqueous emulsions of polyvinyl acetate, carboxymethylcellulose its derivatives and congeners, alginates or plastics dispersions, often used in the preparation of wetlaid webs, may act a primer coats on certain papers.

It is believed that a properly coated mechanical support has bonds in its surface "linked" with the polar parts of the organopolysiloxane material with the latter's oleophilic parts exposed, that is forming the outer "layer".

It is believed that a perfectly continuous layer of elastomer is not essential to the proper working of the invention in every case. However, should some fibers of the porous support material obtrude through the cladding film such could presumably act as a wick for the liquid. It is important to ensure that such "wicking" does not cause wetting of the exposed-to-atmosphere side of the support.

The amount of organopolysiloxane material on the porous support varies with the nature of the substrate, the nature of the liquid contained, the nature of the organopolysiloxane material and the rate of emanation desired. Those are matters that may be determined and balanced by simple experiment by the formulator.

Generally, thin films are sought after, giving a coating of about 0.5 g/m$^2$ of solids. Up to 50 g/m$^2$ based on dry coat weight of organopolysiloxane elastomer may be applied, for example up to 20 g/m$^2$. Preferably, over 12 g/m$^2$ on the same basis is applied; however, 5–8 g/m$^2$ has been used for coating papers with specialist dispersions. Typical coating thicknesses used lie in the range 1 to 1000 microns measured as wet coat. This may reduce partly by penetration of the silicone into the porous substrate, and partly on curing.

Nonetheless some room-temperature curing organo- polysiloxane oligomers or prepolymers such as *SILASTIC 382, Trade Mark a stannous octoate catalysed oligomer and *SILASTIC MDX4-4210, Trade Mark catalysed by a noble metal organometallic compound and supplied by Dow-Corning, require a significantly thick application of approximately 3–4 mm thickness to provide proof against leakage of liquid. Room-temperature curing materials can of course be more rapidly cured by heating in an oven.

A readily available, already-coated substrate for use in certain situations is silicone-coated paper commonly used as a backing for peelable adhesive labels. Certain of these abherent substrates have been found to be useful with some perfume compositions. One porous support for such use is glassine.

The invention may be applied to the controlled release of air freshener liquids, for example perfumes; insecticidal liquids; insect repellents; deodorants; odourising jewellery or personal decorations; corrosion inhibitors, germicidal and medicaments such as respiration aiding liquids.

Compositions to which the present invention is applied include the above treatment materials alone or in combination, in suitable cases, in volatile liquid form. By volatile is meant that the treatment material although liquid is effective in the vapour state. The liquid may evaporate relatively slowly but volatilistion is complete in due course. A proportion of less volatile or relatively non-volatile materials which do not totally evaporate in a given time in the compositions is admissable. Preferably, for a composition intended to be volatilised within about 30 days, it should contain no more than about 10% w/w of such non-volatiles. More particularly such a composition should contain no more than 7.5% w/w of non-volatiles.

The rate of emanation is important in determining the life of devices in accordance with the present invention and this is controlled by the emanator surface area, the chemical and physical properties of the treatment material as well as the chemical and physical nature of the silicone used and the thickness or loading density at which it is supplied to the porous substrate.

A simple test, the so-called "Swelling Test" is indicative of the utility in the present invention of a silicone-liquid combination. The "Swelling Test" is described below with reference to a space reodorant composition, by way of illustration, being the treatment material to emanate from the device: a small weighed piece of cured silicone elastomer is measured and is then totally immersed in the perfume of choice when swelling of the polymer is observable. The difference between (i) the observed dimensions and the original dimensions is expressed as a percentage of the original; (ii) the observed weight and the original weight is expressed as a percentage of the original; usually herein it is the volume percentage increase which is referred to as percentage swellability.

An increase in volume of at least 25% within one week is regarded as typical of a useful silicone for the perfume of choice. A swellability in excess of 100% is considered to indicate a high degree of permeability.

Another useful indicator of permeability of silicones to volatile liquids is the Hildebrand solubility parameter ($\oplus$), the square root of the vapourisation energy per molar volume in each case of the volatile liquid and the silicone. Preferably, the values of the solubility parameters have to be within 2 MPa$^{\frac{1}{2}}$ of each other.

Preferably, the solubility parameter for the volatile liquid for emanation from a device of the present invention lies in the range 10 to 25 MPa$^{\frac{1}{2}}$. It follows that the useful silicones will be in the range 8 to 27 MPa$^{\frac{1}{2}}$.

In order further to illustrate the invention one embodiment thereof is described below with reference to the accompanying drawings in which.

Figure 1:
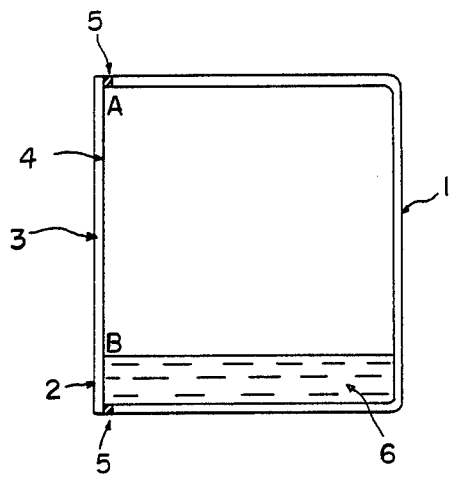
FIG. 1 is a vertical section of an emanator device in accordance with the present invention in one operating position.

Referring to the drawings, an open topped glass container, 1 is closed by a sheet of a porous support, 3 impregnated with a silicone elastomer from its face, 2 that is disposed exterior of the container so that little or none occurs on its opposite face, 4 disposed interior of the container that is the side including A and B. The impregnated porous support, 3 is sealed around its periphery across the container opening with a sealant to provide a liquid proof seal, 5.

A volatile liquid, 6 is contained in the so-closed container, 1. In FIG. 1 the liquid, 6 is in contact with the impregnated porous support, 3; in FIG. 2 the liquid, 6 does not contact the impregnated porous support, 3 unless and until the device is tipped on its side or inverted.

For storage the exterior side, 2 of the impregnated porous support, is protected by a removable sheet of impermeable material, such as aluminium foil (not shown), to prevent wasteful loss of vapour during storage.

Referring now to the device, 1 in the operating position depicted in FIG. 1, volatile liquid, 6 contacts only an edge of the impregnated porous support, 3 below B on the inner face, 4. The porous support 3, absorbs liquid, 6 so that it is constantly impregnated therewith during operation and the free space above the liquid, 6 in the container, 1 is constantly saturated with vapour of the liquid, 6.

Transmission through the impregnated porous support occurs and vapour emanates from the outer surface, 2 thereof in substantially linear fashion over a period of time. This is a consequence of the dynamic equilibrium set up for so long as some liquid, 6 remains in the container, 1. No wetting of the outer surface, 2 is detectable and no liquid, 6 is lost from the container as liquid when the seal, 5 is adequate. A continuous emanation is thus achieved.

When the liquid, 6 is exhausted, the fact is apparent on visual inspection provided the container is constructed of a translucent material.

Figure 2:
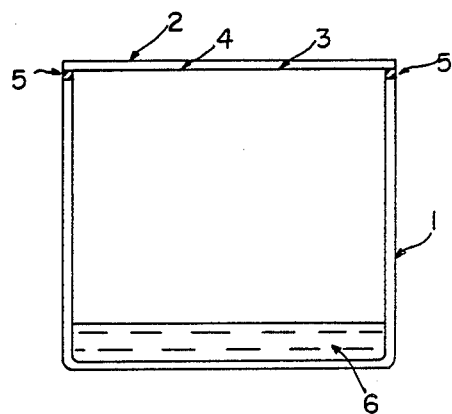
FIG. 2 is as FIG. 1 with the device rotated through a right angle in another operating position.

In an alternative operating position depicted in FIG. 2, the porous support is wetted with volatile liquid, 6 by inverting the container, 1. In this way an intermittent emanation can be produced as and when desired by reinverting the container, 1 whereupon emanation ceases or is significantly reduced when the volatile liquid absorbed by the porous support is temporarily exhausted.

The device can therefore be used as a constant emission device or as an intermittant emission device thus giving a measure of control over rates of emission.

The emanator of the present invention can show considerable savings in silicone by virtue of its relative thinness when distributed over and/or within the porous support.

Devices in accordance with the invention have the advantages of:
(i) an end-of-life indicator in that the reservoir of treatment material may be transluscent so that a user can observe the level of contained liquid by visual inspection;
(ii) where there is no need for a removable-replaceable closure they can be leakproof;
(iii) complete discharge of contents is assured;
(iv) in some cases relatively constant release with respect to temperature variation is achieved;
(v) since wrapping at manufacture need be only a tear-off impermeable strip over the mechanical support, they are easily accessible; moreover beneath the tear-off strip the outer surface is charged with vapour immediately it is uncovered, that is the substance is readily accessible;
(vi) savings in expensive organopolysiloxane material can be shown over the use of blocks or thick webs.

The following examples illustrate slow release perfume containers falling within the scope of the present invention.

EXAMPLE 1

A polysiloxane elastomer prepared by the reaction between parts A and B of Medical Grade Elastomer Q7-2245, Trade Mark (Dow-Corning) was formed at a coat-weight of 20 gm$^{-2}$, by forming a 10% w/w solution of Part A in 1,1,1-Trichloro-ethane, adding a catalytic amount of Part B, and applying the composition to the paper at a rate of 200 gm$^{-2}$. After a period of ambient air-drying to allow evaporation of solvent, the treated paper was placed in an oven at 140° C. for one hour. At the end of this time it was apparent that the coating had undergone a physical change consistent with vulcanisation, that is crosslinking, having taken place.

The treated paper was used to seal the mouth of a small glass container in which had been placed a quantity of "perfume" (reference LS 00253 and supplied by Bush Boake Allen). The method of sealing was that the paper was placed such that the treated side was in contact with the rim of the glass container, and sealed in position using a commercially available acetoxy siloxane elastomeric sealant.

The device was placed in an inverted position, so that the perfume was in contact with the whole of the treated side of the paper and the untreated face of the paper was substantially open to ambient air. After a relatively short period of time, it was evident that perfume was emanating into the surrounding air.

After a further period of one week the perfume was continuing to evaporate into the surrounding air, but the untreated face of the paper was not wetted by the perfume.

EXAMPLE 2

A 5.0 cm length of sintered polyethylene tubing of bore 0.6 cm was immersed in a 1,1,1-trichlorethane solution of the silicone elastomer of Example 1 until degassing ceased. The tubing was allowed to air dry and was then heated in an oven for 1½ hours at 105° C. to ensure curing of the elastomer.

The thus treated tube was used to connect the open ends of a pair of glass phials into one of which had been introduced a volume of perfume.

When the connections were properly made there was no leaking liquid phase perfume; whereas in a similar arrangement using untreated tubing, the perfume flowed out slowly and wetted the outer surface of the tube and ran down the phial.

Emission of vapour increased, as observed by sniffing, each time the device was inverted end for end so that the perfume flowed over and wetted the inner surface of the treated tube as the perfume passed from one phial to the other.

EXAMPLE 3

A polysiloxane elastomer prepared through catalytic reaction by dibutyltin acylate of an aminofunctional polysiloxane with a mixture of silanol and silane (I C I silicone 425 system) was coated onto a blotting paper, density 139 gm$^{-2}$ having oil absorbency 49%, at 500 microns thickness equivalent to 500 gm$^{-2}$. The coating was dried. The treated blotting paper was sealed across the mouth of a circular section glass jar of capacity 120 ml., in which was about 10 ml of a perfume composition (SPRINT perfume LH2283 supplied by Bush Boake Allen). A seal was made using a commercially available acetoxysiloxane elastomeric sealant to provide a peripheral seal, and the coated side of the blotting paper was external of the container. The device was placed so that the blotting paper was vertical and the perfume contacted only the lower part thereof. After a relatively short passage of time it was evident that perfume was emanating into the surrounding air but no wetting of the exterior of the blotting paper was observed.

Following such exposure for 28 days, 70% of the liquid had gone and a fragrance still persisted. During this time no external wetting was observed.

A porous substrate may be constructed in two sheets separated by a thin film of the organopolysiloxane material.

Preferably the side from which application of the organopolysiloxane material is applied is placed into direct contact with the treatment liquid. Further, where a seal between a coated substrate and a treatment liquid container has to be made, generally we have found silicone adhesives to be preferred. Care must be exercised to avoid using sealants which would permit leakage, for example during storage.

An "inner" and an "outer" application of organopolysiloxane material can be envisaged and they may be the same or different in chemical constitution and/or physical form. Thus it may be desirable to have a silicone adhesive on an outer surface so as to secure a vapour impermeable barrier material for the duration of storing. It is clear that for use such impermeable barrier must be removable by a user for use.

Suitable silicone polymers mixed with or including in their structure units of polymer that give rise to heat sealing may be employed to provide a good seal. Where the surface in contact with the container has not been treated sealing may be effected in most cases with the customary compositions used in the packaging Art.

Refillable devices with, for example screw closures are envisaged.

The invention includes within its scope a method for producing vapour from a volatile liquid in which a porous support provided with at least one partly crosslinked organopolysiloxane material which serves to close the pores of the support to passage of the liquid and yet permit passage of vapour is wetted on one side with the volatile liquid the opposite side is freely exposed to atmosphere and vapour emanates from the said opposite side which is not wetted by the liquid. Since silicones are generally noted for their resistance to water, the devices of the present invention find appplication in releasing liquid treatment materials into a body of water in controlled fashion at dosage rates determined solely by the area of the exposed emanating surface.

We claim:

1. A device for containing a volatile liquid and dispensing said liquid as a vapour which comprises a closed container having walls impermeable to said liquid and vapour and at least one wall which includes a porous support provided with at least one crosslinked organopolysiloxane material which serves to close pores in the support to prevent passage of liquid therethrough while permitting the passage of vapour.

2. A device according to claim 1 in which the organopolysiloxane material forms a film over the support.

3. A device according to claim 2 in which the film is continuous.

4. A device according to claim 1 in which the organopolysiloxane material is preponderantly an elastomer.

5. A device according to claim 1 in which the organopolysiloxane material is prepared via room-temperature or low temperature vulcanisation of a prepolymer or oligomer.

6. A device according to claim 5 in which the prepolymer or oligomer has mean molecular weight consistent with a viscosity of up to 1,000,000 mm$^2$/sec at 25° C.

7. A device according to claim 5 in which the prepolymer or oligomer has the mean molecular weigh consistent with a viscosity in the range 100 to 1,000,000 mm$^2$/sec at 25° C.

8. A device according to claim 5 in which the prepolymer or oligomer has at least two silanol end-groups per molecule and the organopolysiloxane material is produced by condensation.

9. A device according to claim 5 in which the prepolymer or oligomer has vinyl or allyl end-groups and the organopolysiloxane material is produced by an addition or chain transfer reaction.

10. A device according to claim 5 in which the organopolysiloxane material is prepared by crosslinking with a hydride-functional siloxane prepolymer containing at least one reactive hydrogen atom per 3 silicon atoms.

11. A device according to claim 5 in which the organopolysiloxane material is applied from aqueous emulsion.

12. A device according to claim 5 in which the organopolysiloxane material is applied from solution.

13. A device according to claim 5 in which the organopolysiloxane material is cured in situ on the support.

14. A device according to claim 1 in which up to 50 g/m$^2$ based on dry coat weight of organopolysiloxane material is applied.

15. A device according to claim 1 in which the organopolysiloxane material has an oil absorbency of at least 10%.

16. A device according to claim 15 in which said oil absorbency is at least 17%.

17. A device according to claim 1 in which the organopolysiloxane material has a solubility parameter in the range 8 to 27 MPa$^{\frac{1}{2}}$.

18. A device according to claim 1 in which the organopolysiloxane material provided presents an essentially oleophilic free surface and the link with the porous support is via polar groups.

19. A device according to claim 1 in which a primer or other pretreatment is used prior to its provision with the organopolysiloxane material.

20. A device according to claim 19 in which the primer is non-aqueous.

21. A device according to claim 19 in which the primer is an aqueous dispersion of polyvinyl alcohol, carboxymethyl cellulose, an alginate or a plastics emulsion.

22. A device according to claim 1 in which the organopolysiloxane material is principally located in or adjacent a surface of the porous support.

23. A device according to claim 22 in which the organopolysiloxane material is located on opposite faces of a porous support.

24. A device according to claim 22 in which the organopolysiloxane polysiloxane material is located between the adjacent faces of a two-part support.

25. A device according to claim 23 in which the organopolysiloxane material on one face of a porous support is chemically of different composition from that on the other face of the porous support.

26. A device according to claim 1 in which the porous support is in the form of a web, sheet, bed or tube.

27. A device according to claim 26 in which the tube is closed ended.

28. A device according to claim 1 in which the porous support is formed of natural or synthetic woven or non-woven fiber, paper products, porous glass, porous plastics, parchment, leather or rubber.

29. A device according to claim 28 in which the porous support is paper.

30. A device according to claim 29 in which the paper carries 5 to 8 gm$^{-2}$ of organopolysiloxane material based on dry coat weight, on at least one side thereof.

31. A device according to claim 28 in which the porous support is sintered polyethylene, sintered polyurethane or an open pored polymer produced by leaching solubles from a moulded or cast body containing such.

32. A device according to claim 28 in which the porous support is a porous plastics film.

33. A device according to claim 28 in which the support is glassine.

34. A device according to claim 1 in which the porous support provided with the organopolysiloxane material is sealed with a removable, vapour impermeable barrier for storage purpose.

35. A device according to claim 1 in which the volatile liquid is a perfume, insecticide, insect repellant, an insect attractant, a higher animal repellant, corrosion inhibitor, a germicidal agent or a medicament.

36. A device according to claim 35 in which the solubility parameter of the volatile liquid lies in the range 10 to 5 MPa$^{\frac{1}{2}}$.

37. A device according to claim 36 in which the values for the solubility parameter of each of the organopolysiloxane material and the volatile liquid differ by $\frac{1}{2}$2 MPa$^{\frac{1}{2}}$.

38. A device according to claim 1 in which the swellability of the organopolysiloxane material in the volatile liquid is at least 25% within 1 week.

39. A method of controlling the dispensing of a volatile liquid as a vapour from a closable impermeable container which method consists in closing the container with a porous support impregnated from at least one side with a cross-linked organopolysiloxane material serving to close the pores of the support to passage of the liquid and to permit passage of vapour, wetting the closure interiorly with the liquid, permitting volatilisation thereof through the closure such that no wetting of the closure occurs on the other side.

* * * * *

UNITED STATES PATENT AND TRADEMARK OFFICE
CERTIFICATE OF CORRECTION

PATENT NO. : 4,898,328

DATED : Feb. 6, 1990

INVENTOR(S) : Fox et al

It is certified that error appears in the above-identified patent and that said Letters Patent is hereby corrected as shown below:

Col. 10, line 2 (claim 24) delete "polysiloxane".

Col. 10, line 41 (claim 36) change "10 to 5 MPa½" to --10 to 25 MPa½--.

Signed and Sealed this

Eighteenth Day of February, 1992

Attest:

HARRY F. MANBECK, JR.

*Attesting Officer*  *Commissioner of Patents and Trademarks*